United States Patent [19]

Jain

[11] 4,322,275
[45] Mar. 30, 1982

[54] FRACTIONATION OF PROTEIN MIXTURES

[75] Inventor: Surendar M. Jain, Watertown, Mass.

[73] Assignee: Ionics Incorporated, Watertown, Mass.

[21] Appl. No.: 197,394

[22] Filed: Oct. 16, 1980

Related U.S. Application Data

[63] Continuation-in-part of Ser. No. 111,144, Jan. 10, 1980, Pat. No. 4,276,140.

[51] Int. Cl.³ .................. B01D 13/02; A23J 1/06; A61K 37/04
[52] U.S. Cl. ............................. 204/180 P; 204/301; 260/112 R; 260/112 B; 260/122; 424/12; 424/36; 424/101; 424/177; 23/902; 128/214 B; 128/DIG. 22; 210/927
[58] Field of Search ............ 204/180 P, 180 R, 301; 260/112 R, 112 B, 121, 122; 424/12, 36, 177, 96, 101; 23/902, 913, 915; 128/214 B, DIG. 22; 210/DIG. 23, 257 M, 22 R

[56] References Cited

U.S. PATENT DOCUMENTS

| | | | |
|---|---|---|---|
| 1,270,271 | 6/1918 | Dorset et al. | 424/101 X |
| 1,335,986 | 4/1920 | Reichel | 424/177 x |
| 1,718,282 | 6/1929 | Fejes et al. | 204/180 P |
| 2,461,505 | 2/1949 | Daniel | 210/645 X |
| 2,710,293 | 6/1955 | Gerlough | 424/177 |
| 3,074,851 | 1/1963 | Knedel | 424/177 X |
| 3,234,199 | 2/1966 | Reid | 424/177 X |
| 3,318,771 | 5/1967 | Jensen | 424/101 X |
| 3,582,488 | 6/1971 | Zeineh | 210/647 X |
| 3,677,923 | 7/1972 | Bier | 204/180 P |
| 3,751,356 | 8/1973 | Takeya et al. | 204/180 P X |
| 3,911,915 | 10/1975 | Seifter et al. | 210/646 X |
| 3,972,791 | 8/1976 | Stern | 204/180 P |
| 3,989,613 | 11/1976 | Gritzner | 204/180 P X |
| 4,043,895 | 8/1977 | Gritzner | 204/301 |
| 4,138,501 | 2/1979 | Chaveron et al. | 204/180 P X |
| 4,204,929 | 5/1980 | Bier | 204/180 P X |
| 4,216,205 | 8/1980 | Radowitz | 424/101 X |

Primary Examiner—Arthur C. Prescott
Attorney, Agent, or Firm—Norman E. Saliba

[57] ABSTRACT

This invention relates to the separation of complex protein mixtures by lowering (desalting) or by raising (salting-out) their electrolytic (ionic) concentration by electrodialysis followed by chilling, pH adjustment, filtration, and/or centrifugation and optionally thereafter restoration of the lost electrolyte or removal of the gained electrolyte and water. This technique is especially adaptable for therapeutic plasma exchange performed in situ for immunepheresis i.e. removal of globulin or immunecomplexes implicated in autoimmune diseases. The techniques are also applicable for antihemophilic factor separation and purification, and separation of proteins from whey.

37 Claims, 6 Drawing Figures

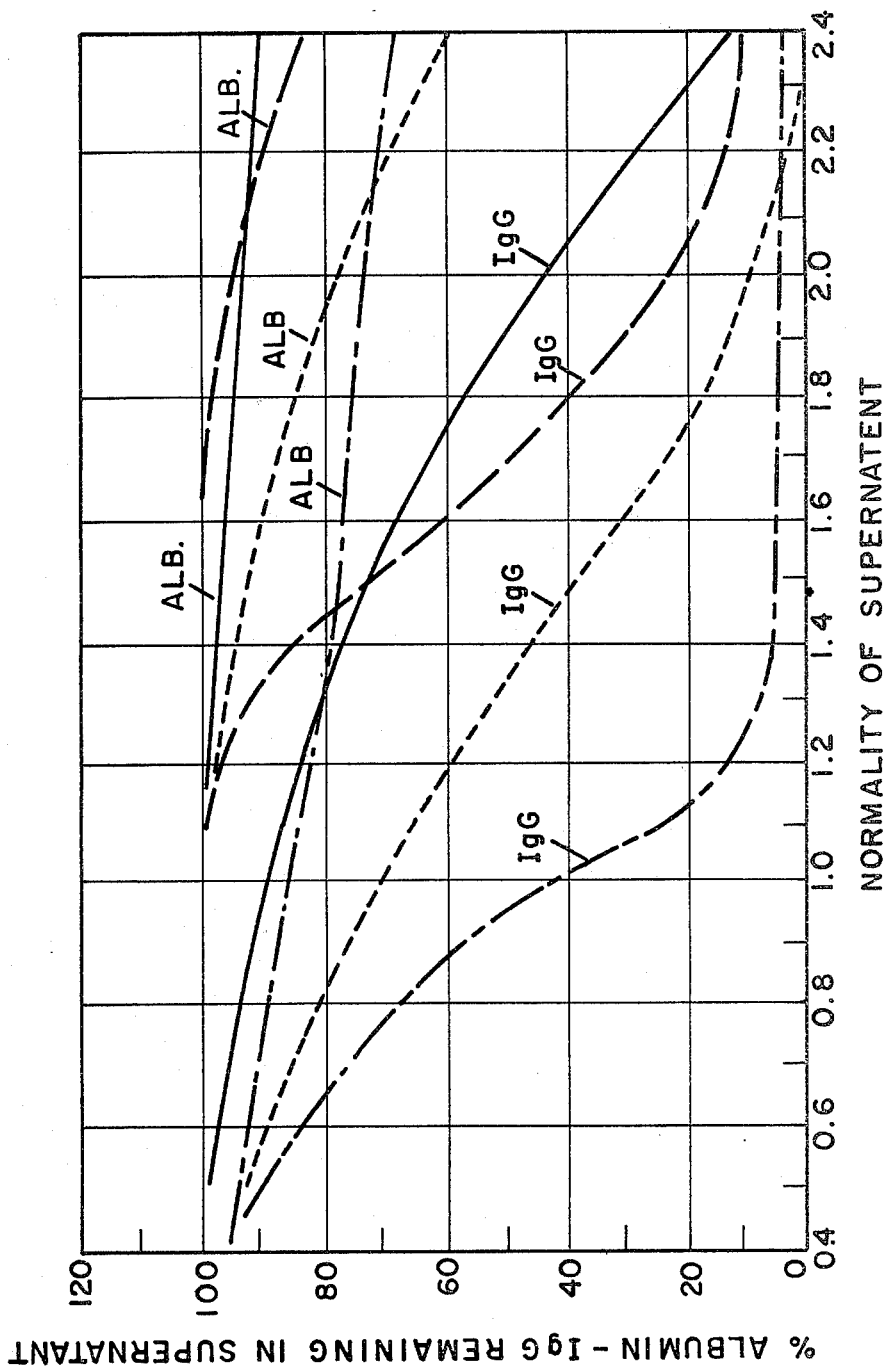

FRACTIONATION OF PROTEIN MIXTURES

This application is a continuation-in-part of parent application Ser. No. 111,144 filed Jan. 10, 1980 now U.S. Pat. No. 4,276,140.

BACKGROUND OF THE INVENTION

Biological fluids such as blood plasma or serum, milk whey, urine, etc. contain a mixture of several proteins. For example, blood plasma contains albumin (3.5-4.5 g/100 ml, M. wt. 66,000), fibrinogen (0.20-0.45 g/100 ml, M. wt 340,000), α-globulins (0.4-1.0 g/100 ml) β-globulins (0.8-1.8 g/100 ml, M. wt. 160,000), IgM (0.06-0.25 g/100 ml, M. wt. 950,000), etc. (Frank W. Putnam, The Trace Components of Plasma, An Overview). The immunoglobulins (Ig's) are very important since they are involved in the protective and defensive mechanisms against infectious organisms. Clinical diseases characterized by imbalances of these systems of proteins for example either in the ability to recognize invading organisms or to recognize indigenous protein or polynucleic acids, have promoted the basic understanding of the clinical aspects of the science of immunity. Abnormal immunological reactions are now known to cause a wide spectrum of diseases. Examples of diseases known to be associated with immune complex reactions include, for example, serum sickness, glomerulonephritis and myasthenia gravis. Plasmapheresis is a technique used to curtail, favorably interfere with or stop the immunopathologic process associated with circulating humoral antibody and/or immune complexes of the plasma. [Glassman, Rationale for Plasmapheresis, "Plasma Therapy" Vol. 1 No. 1, Page 13 (1979).]

A known method is to plasmapherese about 4 liters of blood by centrifugation or cross-flow filtration over a period of 2-4 hours. The plasma removed from the patient in this way is usually discarded and replaced by albumin and either physiological saline or Ringer's solution to make up the protein, electrolyte, and water balance. This is an expensive method. In another method the replacement of the removed plasma is accomplished by giving fresh or frozen pool plasma, and though less expensive, suffers from the risk of transmitting hepatitis virus to the patient. The method of the present invention (referred to as immunepheresis) overcomes these problems by selectively removing immune-globulins, euglobulins or euglobulin antigen complexes causing or resulting from the disease and at the same time restoring the major portions of albumin, electrolyte (salt) and water and thus returning to the patient his or her own plasma (substantially depleted in Ig or Ig antigen complex) containing the proper protein, risk free from hepatitis since no additional albumin or donor plasma is required.

Antihemophilic factor or antihemophilic globulin (Factor (AHF) VIII, AHF or AHG) is one of the constituents involved in the coagulation of blood. A hereditary disorder of blood coagulation, hemophilia, results in profuse bleeding in joints, muscles or internal organs as a result or minor trauma. This disease appears to be due to a deficiency of a specific plasma protein AHF. Affected individuals frequently require therapy following minor accidents. In case surgery is required, clotting abnormality is corrected by fresh plasma transfusions or by injection of Factor VIII concentrate, the latter being preferred since it avoids hyperproteinemia and possible kidney dysfunction resulting from large volume transfusions.

Prior art methods for production of AHF consist for example, of taking pool-plasma, forming a cryoprecipitate, centrifuging the precipitate which mainly consists of a mixture of AHF and fibrinogen, removing fibrinogen and thereafter employing lyophilization to produce AHF concentrate. These methods suffer from the disadvantages of being long and cumbersome and of having the risk of transmitting hepatitis because of the pool-plasma source. Also the presence of fibrinogen as an impurity makes it difficult for the AHF concentrates to go into solution. In addition, due to an elapse of several days between donation and use there is a considerable loss of AHF activity. An AHF unit is defined as the activity present in 1 ml. of average normal pooled human plasma which is less than 1 hour old (100% AHF level). Thus after six hours the loss in activity in extra corporeal liquid plasma can be as great as 80%. A rapid method of processing AHF would prevent this loss of activity. The apparatus and methods of the present invention overcome these problems by being suited to an on-line real-time method. Therefore the recovery of AHF can be as high as 4 to 5 times that of the present, long elapsed time methods. The present invention is adaptable to a smaller pooled source, e.g. 2-3 hepatitis-free members of the hemophiliac's family can donate plasma and have the AHF recovered on site within a short time thereafter thus providing a hepatitis-free AHF of very high activity. On-line methods of this invention can also be used to recover Factor VIII from donors during plasmapheresis.

The basic techniques employed in the present invention, i.e. plasmapheresis and electrodialysis are each well known in the prior art. The novel combination of the techniques described herein produces a synergism i.e. it increases the efficacy of each step and of the combination in an unexpected manner and makes them extremely useful especially for in situ real-time therapeutic use for patients for whom removal of Ig's or complexes thereof is required.

The methods of the present invention will be described using plasma and whey proteins as preferred examples but the scope of this invention can also be applied to other biological fluids or other proteins without limiting the scope of the invention. The use of electrodialysis for salting-out or alternatively desalting to obtain protein separations can serve as very efficient tools in the hands of protein chemists.

THE INVENTION

The present invention relates to the application of electrodialysis for separating aqueous protein mixtures into fractions having intrinsically distinguishable compositions as determined by well known physical or chemical procedures. The invention involves the fractionation or partial resolution of protein mixtures and restoration thereafter of their salt and water balances. It relates not only to the fractionation by salt depletion (desalting) but also by salt addition (salting-out). The protein mixtures comprise principally (but not exclusively) plasma, serum or their derivative fractions. The electrodialysis process employed in desalting removes dissolved salts (ions) and consequently euglobulins or their complexes are substantially precipitated by the reduction of ionic concentration, if desired combined with temperature and/or pH changes. Upon removal of salts, the interaction of the salt ions with the ionizable groups of the proteins is apparently reduced, allowing interaction among the euglobulin molecules hence precipitating them. Albumin and other proteins which are not euglobulins in nature do not precipitate at the (low) salt concentrations which are effective for euglobulins and therefore remain in solution for subsequent return to the patient or for recovery. After removal of euglobulin turbidity (or precipitate) the ionic concentration of the plasma may optionally be returned to substantially its initial value by using the salt depleted plasma as the salt receiving stream in an electrodialysis stack or module. The salt depleted plasma is thus substantially restored in electrolytes (and water) and can be given back to the donor or to the patient without any further modification of the salt or water content.

In the salting-out embodiment of the process, salt is brought into the protein mixture to cause the various proteins to preciptate out one-by-one as the ionic strength increases. The salting-out agents in this group apparently operate by decreasing the activity of the water in the solvent mixture, thereby dehydrating the hydrophilic groups of the protein molecules and thereby causing precipitation of proteins.

In a third embodiment of this invention, use is made of the addition of certain agents e.g. metal ions, small anions and polyanions (polyphosphates etc.) which tend to cause precipitation (turbidity) apparently by a different mechanism whereby the electrostatic charges of a few critical groups on the protein seem to be effected. Since ionization of these critical groups is required to maintain a normal state of hydration of the protein molecule, precipitation is often induced by the mere effect of compensating the net electrical charge of the protein molecules. Such agents are needed only in low and definite concentrations since the mechanism is not a bulk effect. Electrodialysis can accomplish this in an excellently controlled manner.

The prior art utilized direct bulk addition of these agents thus causing powerful localized effects. With electrodialysis, all the above described embodiments of the present invention can be handled easily and fractionation can be easily controlled or in some cases even enhanced.

More specifically, certain embodiments of the present invention comprise processes for fractionating liquid protein mixtures containing dissolved salt or/salts therein by employing electrodialysis (ED) apparatus having one or more pairs of salt receiving and salt diluting chambers, separated from each other by ion-selective, neutral (non-selective) or combination of neutral and ion-selective membranes. In one embodiment, electric current is impressed between end electrodes to reduce the salt content of a protein mixture located in the salt diluting chambers by transfering the salts from such chambers to adjacent receiving chambers. Such desalting is continued until turbidity is produced. The production of turbidity may be facilitated if desired by prior, simultaneous or subsequent alteration of pH and/or temperature. Substantially desalted protein mixture from the diluting chambers is collected and treated to separate and remove therefrom one or more of the protein components causing turbidity. Optionally thereafter the resulting salt depleted protein mixture is optionally passed into the salt receiving chambers whereby the salts entering such chambers from the adjacent diluting chambers will substantially restore to the desalted protein mixture its original salt and water content. Such renormalization is desirable if the protein mixture is blood plasma which it is desired to return to the donor.

The process described above is especially efficacious where the liquid protein mixture is blood plasma or serum, where the protein components removed are globulins and/or their complexes and in which at least one of the membranes in every pair is ion-selective.

An alternative method of practicing the above described embodiment wherein at least one of the membranes in every pair is ion selective is to collect the desalted protein mixture from the diluting chambers of the ED stack, remove one or more of the precipitated proteins from the desalted protein mixture and thereafter recycle the resulting salt depleted, protein depleted mixture back into the prior diluting chambers. A direct current of such polarity is applied so that the prior diluting chambers now containing a salt depleted mixture become salt concentrating or receiving chambers and the former receiving chambers containing salts removed in the first part of the procedure become diluting or salt depleting thus substantially restore the original salt and water content of the desalted protein mixture.

In another embodiment of the invention, the said precipitation or turbidity may be caused by salting-out i.e. by the addition to the protein mixture of a salting-out agent. These agents include for example, sulfate salts ($Na_2SO_4$, $K_2SO_4$, $(NH_4)_2SO_4$, $MgSO_4$ etc.), acetate salts (sodium or potassium acetate etc.) citrate salts (sodium or potassium citrate etc.) chloride salts (NaCl, KCl, $MgCl_2$, $CaCl_2$, $LaCL_3$ and other substantially non-toxic, soluble salts. The electrodialysis apparatus used is similar to the first described case; the salt enriched protein mixture in which turbidity has occurred due to salting out by an agent, for example, $Na_2SO_4$, is collected and treated to separate and remove therefrom the one or more of the protein components which cause turbidity. The salt supplying (depleting) stream will contain salting-out agent or alternatively the salt enriched plasma obtained after removal of the precipitate. Thus at essentially the same time, both operations can be accomplished i.e. removal of the precipitating or salting-out agent and the addition of the said agent to cause salting-out. The salt depleted protein stream may then be sent back to the source, optionally after making up the electrolyte balance to substantially its original salt and water content.

The salting-out process described above is especially adaptable where the liquid protein mixture is blood plasma or serum and where the protein components removed are γ-globulins and/or their complexes. ED can add the precipitating agent at a controlled rate, a very important factor. A slow rate of addition of the precipitating agent leads to formation of crystalline protein precipitates of greater protein purity which have far less absorbed contaminants compared with the finer flocks of proteins carried down by the rapid addition of the precipitant which may contain proteins which would not precipitate upon slow addition.

In still another embodiment of this invention the precipitation may be caused by alteration of pH by ED to bring the pH to substantially the iso-electric point (pI) of a certain group of proteins e.g. γ-globulins in case of blood plasma. Salting-out can be accomplished at a lower salt concentration if operated near the isoelectric point of the protein. Precipitation by desalting can be accomplished at a higher salt concentration if operated near the isoelectric point.

In a further embodiment of this invention, protein fractionation can also be carried out by the addition of e.g. zinc glycinate (final concentration of about 20 mM) at a pH of about 7.2 by ED. The zinc ion ($Zn^{++}$) causes precipitation of the various proteins ($\gamma$-globulins, fibrinogen, etc.) in plasma without causing removal of albumin. This method is similar to the above mentioned salting-out embodiment in that the diluting compartment is freed of zinc salt and the concentrating compartment containing the protein mixture is enriched to cause precipitation. The amount of $Zn^{++}$ needed is very small when compared to many other salting-out agents since the mechanism of precipitation apparently consists in merely compensating the net negative electrical charge of the molecule, the balance of charges of the remaining ionogenic groups being zero, the essentially neutral protein molecule is apparently not capable of attracting sufficient amounts of water to remain in solution.

Some of the techniques and embodiments described hereinabove may be combined which will be obvious to those skilled in the art. For example in the separation of certain $\gamma$-globulins from plasma, a direct addition of salting-out agent can be considered in combination with electrodialysis to remove the added salt to recover a relatively rich albumin solution (after removal of globulin precipitate).

In the examples $Na_2SO_4$ is employed as the preferred salting-out precipitating agent but this should not be considered as limiting. Other salts can be used and also their mixtures to refine the fractionation process.

DETAILED DESCRIPTION

Electrodialysis (ED) is widely practiced for desalting of aqueous solutions: brackish water, whey milk (U.S. Pat. Nos. 3,433,726; 3,447,939; 3,595,766; 3,757,005; 3,754,650 etc.). These patents are concerned only with reducing the salt content of a liquid rather than using the ED process in a complex scheme of fractionating and subsequently rebalancing the salt and water content of a mixture of proteins intended for example, for therapeutic use as in cases of plasmapheresis.

Desalting by ion exchange column technology has been used in the past to cause precipitation and thus fractionation of plasma proteins (U.S. Pat. Nos. 3,234,199; 3,073,744). This process however has limited flexibility and the columns are difficult to handle, clean and sterilize when employed under conditions necessary for protein fractionation.

It has now been discovered that electrodialysis can be used not only in the fractionation of proteins as a result of desalting, but also can be employed in a salting-out process and also in a process to restore the electrolyte (salt) and water balance of the resulting processed protein mixtures. The resulting protein is thus ready to be returned to the donor or to a patient with substantially its original salts. The combination of the techniques outlined herein include as essential steps the electrodialysis of the protein mixture, (optionally combined with temperature and pH alteration) and separation of certain precipitated proteins, thereafter the optional substantial restoration of the salt and water balance of the original mixture. This novel method increases the efficacy of each step in an unexpected manner and makes the process extremely useful especially for in situ real-time therapeutic use for plasmapheresis patients where removal of globulins or their complexes is required along with the restoration of essentially the original plasma. By this method, not only is the expense of albumin and salt replacement avoided but also the risk of transmitting hepatitis inherent in the giving of fresh or frozen pool plasma.

BRIEF DESCRIPTION OF DRAWINGS

In a first embodiment of fractionation by desalting, process and apparatus will be hereinafter described by referring to FIGS. 1 and 2 where like parts are referenced with like numerals. In the Figures the fluid under treatment is described with respect to blood plasma but it can be understood to be any other protein mixture.

red and white cells and platelets) (3) previously separated from the plasma. This restored protein mixture (12) can then be given back to the patient (14) substantially without outside addition of albumin or electrolyte. Thus this process is essentially closed, self sufficient, and capable of in-situ real-time operation for therapeutic plasma exchange.

If the temperature of the plasma during electrodialysis is maintained in the range of about 0° to 40° C., if the velocity of the protein mixture in the diluting chambers is in the range of 3 to 40 cm/sec. and the ratio of current density (CD) in ma/cm² to protein solution conductivity (K) in milli Siemens/cm,(CD/K) is kept in the range of 0.1–10, pH changes in the protein will not be substantial and the precipitate so formed (even on relatively complete desalting) will be such as to substantially avoid plugging the chambers of the ED stack. (It should be noted that one mille Siemen equals one milli mho.

Figure 1:
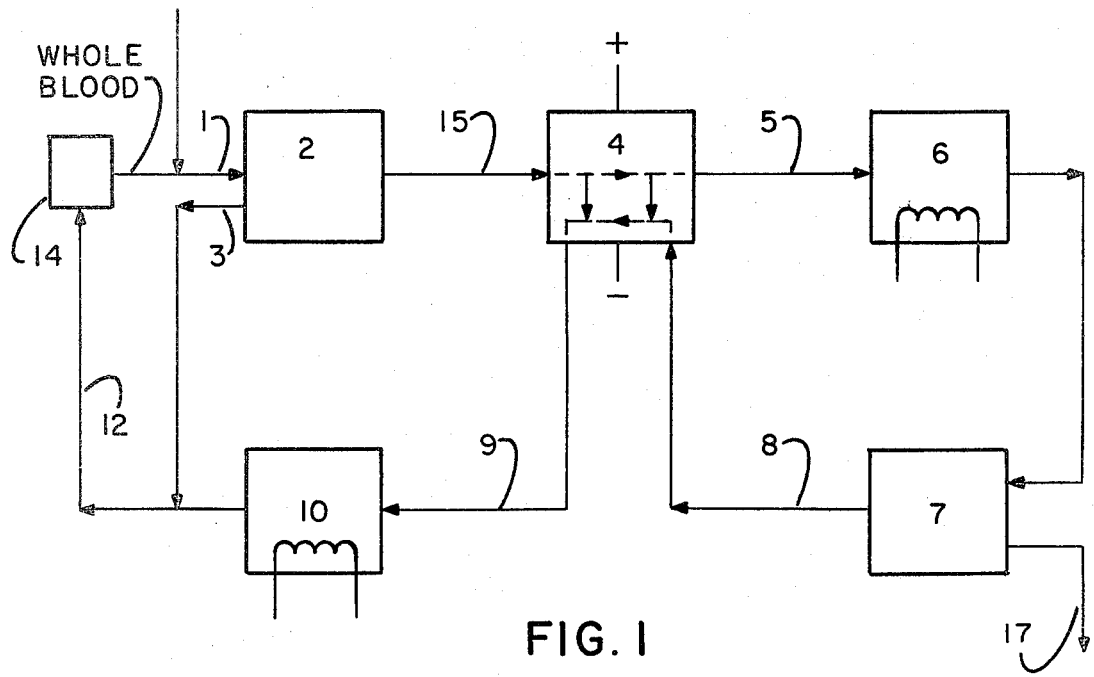
As shown in FIG. 1, citrated or heparinized blood (1) is ultrafiltered and/or centrifuged (2) to separate out the cell components (3), or any other suspension [referred to as formed elements (FE)] and the remaining plasma (15) is sent to an electrodialysis (ED) stack (4) such as that commercially available from Ionics, Inc. Watertown, MA. Electrodialysis equipment and their methods of operation are more fully described in U.S. Pat. Nos. 2,848,403; 2,863,813; 3,003,940; 3,341,441; 4,115,225 and others. Such a stack normally comprises one or more pairs of concentrating and diluting chambers separated by alternating anion and cation exchange membranes. Ion selective membranes can also be replaced under some circumstances by essentially electrically neutral membranes. Thus the anion membrane can be replaced by a neutral membrane if reduced current efficiency for ionic transfer can be tolerated. The chambers are located between anode (+) and a cathode (−). An electrolyte solution is preferably passed through the cathode and anode chambers to conduct current across the concentrating and the diluting chambers. The electric current is passed until at least incipient turbidity is produced, or until such turbidity will be produced when the temperature is reduced and/or the pH is adjusted to substantially the pI of the least soluble protein. Usually a concentrating chamber isolates the electrode solutions from the product or diluting chambers. The membranes are generally but not necessarily selected so as to minimize transfer of low molecular weight compounds such as blood sugars. The flow rates through the stack and the applied electric current are regulated so that excessive changes in pH are avoided. Plasma is passed into and through the diluting chambers and by impressing a direct current across the electrodes, the salt or ionic content of the plasma is reduced due to the passage of salt into the adjacent concentrating chambers (not vertical arrows in stack) which chambers may be primed if desired initially with a small amount of plasma or albumin. The resulting substantially desalted plasma (5) is collected from the diluting chambers (not shown) and passed into means for separating and removing one or more proteins forming turbidity (globulins or their complexes in this case). The separating means may, for example, consist of a heat exchanger (6) to lower temperatures, pH adjustment and centrifuging and/or ultrafiltration apparatus (7). After removal of the turbidity or precipitated globulins (17) or other proteins, the salt depleted mixture (8) is passed into and through the concentrating chambers (not shown) of the ED stack (4) thereby allowing it to receive the salts from the adjacent diluting chambers (note vertical arrows) and hence restoring substantially the original salt content of the mixture. This salt restored mixture (9) is next optionally passed through a heat exchanger (10) to adjust the mixture to approximately body temperature where necessary, and then supplied with the formed elements (e.g.
Figure 2:
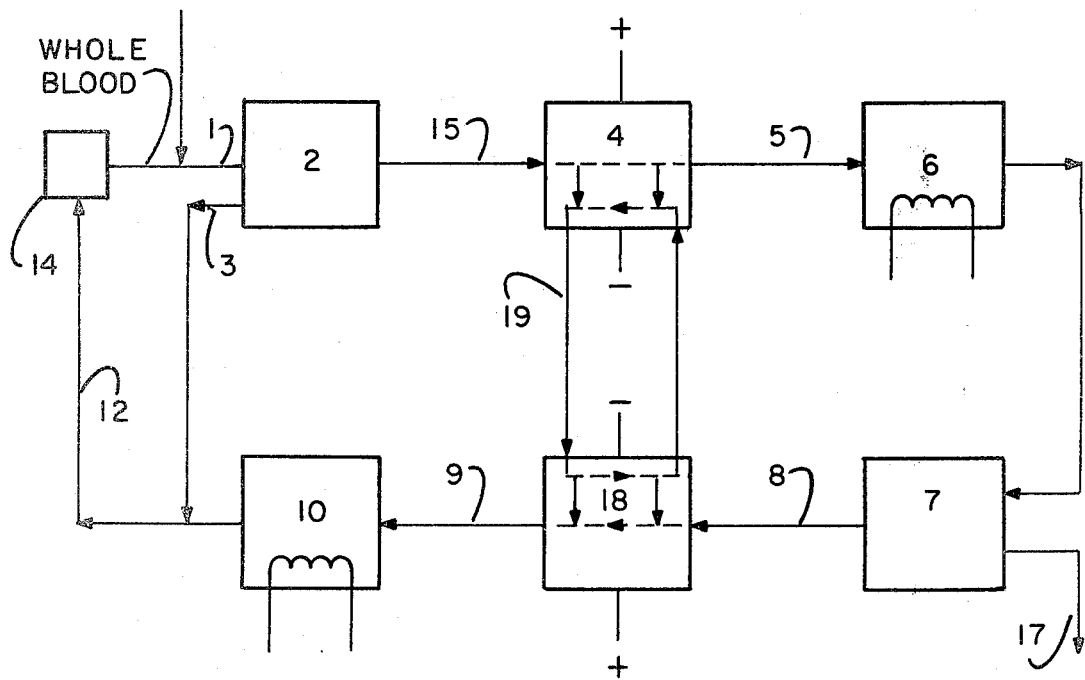

Another embodiment of the apparatus and process of this invention is shown in FIG. 2. The fluid is again plasma (1) but can be any other aqueous, fluid protein mixture. (citrate or heparin may or may not be added to minimize plasma coagulation during processing.) The plasma whether or not heparinized or citrated is ultrafiltered or centrifuged (2) to remove turbidity and then sent to ED stack (4) similar to that described in Example I. Plasma is introduced into the diluting chambers (not shown) and on passing a direct current across the stack, salts from the plasma are transferred (note vertical arrows) to the concentrating chambers. The salt depleted mixture (5) from the diluting chambers is passed through heat exchanger (6) to chill the plasma and the precipitate formed (17) is separated by an ultrafilter or a centrifuge (7) or similar device. The desalted supernatant (8) is then fed to the salt concentrating chambers (not shown) of an electrodialysis stack (18). For this second ED operation another ED stack (18) is shown, in practice it can be the original ED stack (4) where the former concentrating stream (19) of the ED stack (4) forms the diluting stream. The polarity for ED stack (18) may be the reverse of ED stack (4). This second stage ED (18) causes the salts from the former concentrating stream (19) to return to the desalted plasma whereby the salt balance is restored. This renormalized plasma (9) is then passed through heat exchanger (10) and the blood cells or FE (3) are then added. The thus processed blood can be given back to the donor or other patient (14).

EXAMPLE I

This example illustrates the restoration of the electrolyte and water balance of a desalted plasma using a fresh plasma in the dilute stream.

Apparatus used was a laboratory electrodialysis stack using only one cell pair (i.e. one diluting and one concentrating chamber defined by ion-selective membranes) located between terminal electrode chambers. A 0.2 N $Na_2SO_4$ solution was used for the electrode streams to conduct the direct current. A volume of 360 ml of citrated otherwise fresh plasma was used in the diluting stream and 340 ml of desalted plasma was used in the concentrating stream. The linear velocity of the diluting stream was about 25 cm/sec., the temperature was maintained at 15° to 20° C. and the flow rates at 90 ml.min per cell pair. The effective cell area was about 220 cm². The progress of the run is summarized in the following table:

| CD/K | Time (min.) | Amps | Diluting stream (citrated fresh plasma) | | | Conc. stream (desalted plasma) | | |
|---|---|---|---|---|---|---|---|---|
| | | | Conductivity values (K) | pH | vol. | Conductivity values (K) | pH | vol. |
| 4.7 | 0 | 17 | 16.500 | 8.2 | 360 | 0.030 | 5.2 | 340 |
| 4.7 | 6 | 8.8 | 8.600 | 7.4 | 352 | 8.500 | 7.2 | 347 |
| 4.7 | 12 | 4.4 | 4.300 | 6.9 | 347 | 12.400 | 7.7 | 350 |
| 5.0 | 25 | 0.9 | 0.825 | 6.1 | 344 | 15.600 | 8.0 | 353 |
| 27.5 | 35 | 0.2 | 0.033 | 5.2 | 342 | 16.400 | 8.3 | 355 |

Thus the desalted plasma in the concentrating stream has been brought back to a conductivity value comparable to the original unsalted citrated plasma; and the water balance has been restored.

EXAMPLE II

Although the ED stack employed in example I contained ion-selective membranes (anion and cation types), the combination of ion-selective membranes with neutral (non-selective) membranes may also be used. In this example the stack of example I had its anion selective membrane replaced by a neutral membrane comprised of regenerated cellulose. Other type neutral membranes well known in the art, such as reverse osmosis or dialysis type membranes could also be used if so desired. Neutral membranes have the disadvantage of not being as efficient as as ion-selective membranes. However, in processes where the energy input is not a significant consideration, such membranes can then be utilized to advantage.

In this example the stack containing the regenerated cellulose membrane was operated using substantially the same solutions and conditions as noted in example I. The following table summarizes the course of this run:

| CD/K | Time (min.) | Amps | Diluting stream (fresh plasma) | | | Conc. stream (desalted plasma) | | |
|---|---|---|---|---|---|---|---|---|
| | | | Conductivity (K) | pH | vol. | Conductivity (K) | pH | vol. |
| 3.3 | 0 | 12.0 | 16.500 | 8.2 | 360 | 0.050 | 5.3 | 340 |
| 3.3 | 14 | 6.2 | 8.700 | 7.4 | 350 | 8.480 | 7.4 | 350 |
| 3.3 | 27 | 3.1 | 4.300 | 6.9 | 342 | 12.390 | 7.7 | 355 |
| 3.3 | 57 | 0.6 | 0.830 | 6.1 | 337 | 15.450 | 8.0 | 360 |
| 23.3 | 80 | 0.2 | 0.039 | 5.2 | 334 | 16.420 | 8.2 | 363 |

Here again, the desalted plasma has been restored to a conductivity comparable to the original fresh plasma and has also had the water balance restored. It will be noted that the increased time of operation (80 minutes) was due to the current efficiency being considerably less for the combination of neutral and cation exchange membranes.

EXAMPLE III

This example is similar to the example I above except that the desalted plasma is used in the original diluting stream of example I and a water solution containing the removed salts from a prior desalting run is used in the original concentrating stream. The polarity of the current is reversed (thus converting the original concentrating chambers to diluting chambers and the original diluting chambers to concentrating chambers) and the salts from the salt water stream are transferred to the desalted plasma (now the concentrate stream) to bring the salts of the plasma back to its original concentration.

EXAMPLE IV

This example illustrates the removal of immune globulins (Ig) as a function of the degree of desalting.

The apparatus of example I was used with 200 ml of heparinized human plasma employed in the diluting chamber. The temperature was in the range of 10°–26° C. and the CD/K value used was approximately 4 (ma/cm²/mS/cm). A fluid velocity of 25 cm/sec. was employed. The following table summarizes the results and shows that about 50% of the total Ig's are removed while albumin removal is substantially unaltered after 99.7% desalting.

| Time (min.) | pH | Conductivity | % Desalting | Proteins remaining in supernatant (mg/100 ml) | | | |
|---|---|---|---|---|---|---|---|
| | | | | IgG | IgA | IgM | Albumin |
| 0 | 7.55 | 15.280 | 0 | 820 | 115 | 72 | 4,410 |
| 0 | 7.55 | 13.720 | 0 | 750 | 85 | 50 | 3,900 |
| 5 | 7.35 | 7.020 | 48.80 | 780 | 80 | 46 | 3,900 |
| 8 | 7.10 | 3.710 | 72.96 | 700 | 75 | 36 | 3,900 |
| 10 | 6.55 | 1.310 | 90.60 | 630 | 75 | 24 | 4,100 |
| 13 | 5.40 | 0.447 | 96.70 | 570 | 55 | 12 | 4,000 |
| 15 | 5.20 | 0.190 | 98.60 | 450 | 50 | 10 | 4,000 |
| 17 | 4.90 | 0.047 | *99.70 | 410 | 40 | 16 | 3,900 |
| 19 | 5.00 | 0.028 | 99.80 | 410 | 45 | 12 | 3,800 |
| 20 | 5.10 | 0.022 | 99.84 | 410 | 45 | 10 | 3,800 |

*Summary of % Ig's Removed After 99.7% Desalting

| | | % removed | % removed (corrected for water transfer) |
|---|---|---|---|
| IgG | = | 45.3 | 46.7 |
| IgA | = | 52.9 | 55.9 |
| IgM | = | 68.0 | 71.4 |
| Total Ig's | = | 47.3 | 49.7 |

EXAMPLE V

This example illustrates a further embodiment of the invention, where alteration of pH to substantially the isoelectric point of a protein which it is desired to remove can assist its precipitation. Continuation of the desalting of the plasma resulting from example IV will bring the pH down to the isoelectric point (pI) of albumin (about 4.9) thus causing its precipitation. The albumin precipitate is separated by filtration and then resuspended by the addition of salt. This addition is accomplished using ED by making the albumin rich material as the salt concentrating stream thus resulting in a 3–5% isotonic albumin solution. This albumin is essentially free of immunoglobulins and their complexes and can be used as a plasma expander. Thus this is a preferred method for those cases where more than 40–50% removal of immune globulins is desirable for "immune-pheresis" (removal of immunoglobulins) for autoimmune diseases.

In another embodiment of the invention, fractionation is achieved by "salting-out" i.e. the use of salts such as $(NH_4)_2SO_4$, $NA_2SO_4$ etc. brought into the protein mixture by electrodialysis. The various proteins will precipitate out at different salt concentrations and thereby lend themselves to fractionation. A distinct advantage of accomplishing this by ED instead of by direct addition of salts is that ED allows more controlled addition of salts, thus avoiding local concentration gradients. Electrodialysis "salting-out" is also much faster when compared to dialysis is alone where only diffusion (and not an electric potential) is the driving mechanism. Comparable fractionation is achieved by ED at a much lower salt content compared to either addition or dialysis addition of salt.

Figure 3:
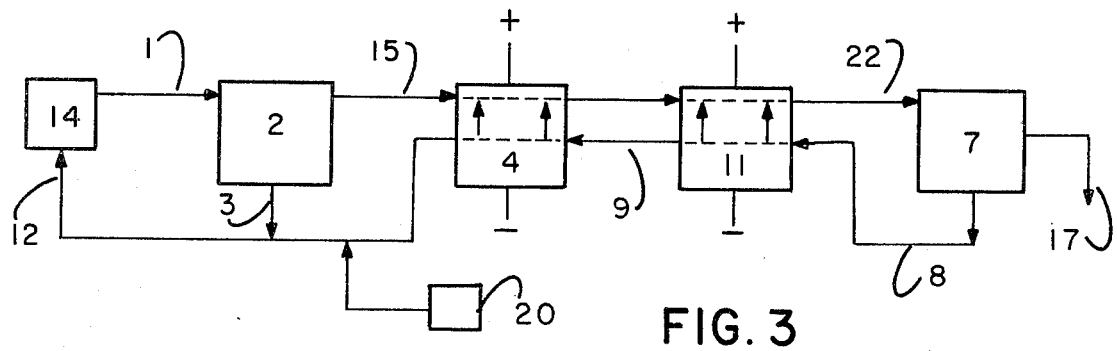
Figure 4:
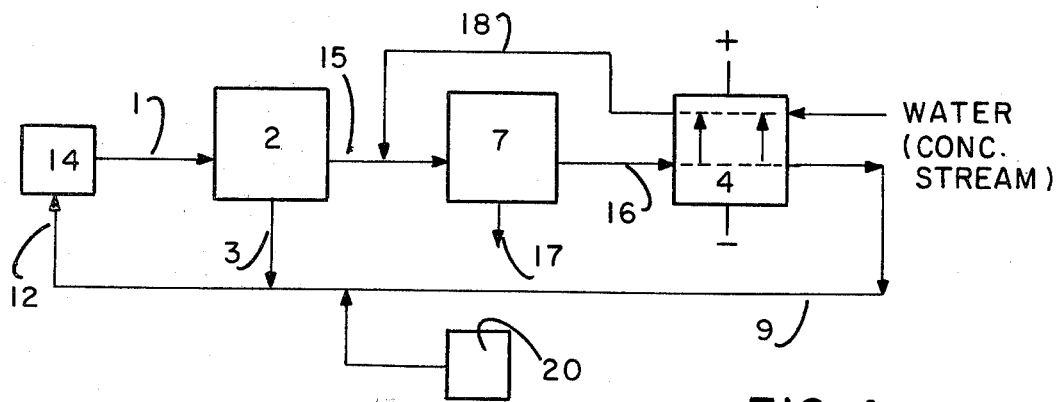

The process and apparatus employed for salting-out will be further described hereinafter for the fractionation of blood plasma protein but is not to be understood as limited to plasma only. Two of the "salting-out" embodiments are shown in FIGS. 3 and 4. As shown in FIG. 3, fresh plasma (15) is pumped as the concentrating stream (salt receiving stream) through two electrodialysis stacks (4) and (11). The resulting salted-out plasma (22) is passed into separation means (7) such as a centrifuge where removal of any precipitated protein (17) is accomplished. The resulting supernatant (8) which becomes the diluting stream to the ED stack (11) is essentially an albumin filtrate containing the salting out agent (such as $Na_2SO_4$) from which a precipitated protein fraction (17) has been removed (e.g. immunoglobulins and fibrinogen). This stream is made to give up its salt (note the direction of vertical arrows) when a current is impressed across the ED stack, that is, transfer the salting-out agent to a fresh plasma stream (15) thus causing the precipitation of certain proteins (globulins) from said fresh plasma stream. In turn this dilute stream (8) becomes depleted of salt and becomes essentially an albumin solution. The final or polishing ED stack (4) is shown separately but it can be part of a single ED stack. This final polishing step may not be required where the product (9) is allowed to have salts which are not objectionable for infusion. A make up electrolyte (20) may be needed if the polishing ED step is required. Thus such a process is compatible with in situ operation for therapeutic plasma exchange and can be carried out not only in batches but also continuously.

Another variation of the salting-out embodiment of this invention is shown in FIG. 4. Here the salting-out agent (salt solution) is added directly to the plasma (15) causing immunoglubulins to precipitate whereby they are separated (7) and removed (17) as by filtration. The resulting plasma (16) employed as the dilute stream is desalted by ED stack (4); with the concentrating stream (18) becoming essentially a solution of the salting-out agent. This concentrated solution (19) can be added directly to fresh plasma (15) in a closed loop fashion. Electrolytes (20) and formed elements (3) may be added to the desalted albumin solution (9) before administering the solution (12) back to the donor or patient (14). Although $Na_2SO_4$ is preferred as the salting-out agent it must be understood that this invention is not limited to it. Other salts and their mixtures may be used such as $K_2SO_4$, $(NH_4)_2SO_4$, sodium citrate, phosphates, NaCl, KCl, acetates, etc. and their mixtures. The amount of salt added will of-course depend upon the fractionation desired. The following example illustrates the separation of IgG from albumin.

EXAMPLE VI 300 ml of plasma was warmed to 28°–37° C. and a saturated solution of $Na_2SO_4$ (approximately 6 N) at 28°–37° C. was added at a rate of 10–15 ml/min. while constantly and rapidly stirring the plasma mixture. The amount of albumin and globulins (IgG) remaining in the supernatant was determined during the salt addition as a function of salt (electrolyte) concentration in the supernatant.

FIG. 5 compares the results using various methods of adding $Na_2SO_4$ electrolyte and shows the approximate protein fractionation (albumin and IgG's) occurring at different electrolyte strengths. Also specifically shown is the fractionation curve resulting when a salt mixture (6 N NaCl and 6 N $Na_2SO_4$) was employed. A comparison of salting-out by electro-dialysis, dialysis and direct salt addition is also illustrated.

The results show that to obtain about 80% removal of globulins (IgG's) from fresh plasma requires a 1.8 N. salt ($Na_2SO_4$) concentration in the plasma (supernatant) in the case where direct salt addition is employed. Under these conditions however, there was also a simultaneous removal (a loss) of about 15% albumin. Where the direct addition employed a salt mixture ($Na_2SO_4$+NaCl) an 80% removal of globulins occurred at about a 2.05 salt normality accompanied by only a 5% removal of albumin. Where the addition of salt ($Na_2SO_4$) is accomplished by use of dialysis an 80% globulin removal was noted at about a 2.3 salt normality but at a loss of about 10% albumin. In comparing the use of salt addition by electrodialysis (ED) it is noted that there is a 95% removal of globulins at a much lower salt normality (1.2 N) with less than 15% loss of albumin. In summary it appears that more complete removal of globulins accompanied with smaller losses of albumin can be accomplished at the lower salt normalities when the salt addition is performed by electrodialysis. An alternate procedure where so desired is to employ a combination of direct addition or dialysis of the salting out agent thereafter followed by ED treatment to remove the added salts therefrom.

EXAMPLE VII

This example illustrates the separation of antihemophilic factor (AHF) and fibrinogen from the plasma. Since the activity of AHF is time and temperature sensitive, the separation is carried out at a low temperature (4° C.). One procedure applied in the separation is lowering the ionic strength of plasma preferably by ED desalting to cause the precipitation (separation) of fibrinogen and AHF, later resolubilizing the precipitate in for example, 0.15 N NaCl and thereafter subjecting the resulting resolubilized liquid once again to ED to lower the ionic strength thus causing the precipitation (and separation) of AHF from fibrinogen. Alternatively after resolubilizing, the latter separation can be caused by specific adsorption of AHF on anion exchange column or by gel permeation techniques.

A second procedure consists of the direct salting out of AHF at an appropriate salt strength. These procedures are also applicable for on line as well as off line use as in the case of immunepheresis.

Another embodiment of this invention is the application of ED to the fractionation of plasma proteins using small amounts of low toxicity heavy metal ions such as zinc diglycinate as the precipitating agent. The plasma is first partially electrodialyzed to remove clotting factors which become precipitated during the desalting. These precipitated factors are removed and the resulting supernatant is passed through the salt concentrating compartments of an ED stack containing zinc diglycinate in the diluting compartments. On application of a electrical potential a controlled amount of zinc diglycinate is transferred into the concentrating compartments to give an ionic strength of about 0.10 normal in the supernatant. The operation is carried out at about 0°–4° C. and at a pH of about 7.0–7.2. This results in the formation of a precipatate consisting essentially of globulins with a supernatant rich in albumin. The supernatant can be clarified of the added zinc by desalting by ED after bringing the pH down to about 5.1–5.8 by suitable addition of a buffer.

Aluminum chloride may also be substituted for zinc diglycinate for fractionally precipitating all proteins except γglobulins. The direct addition of an equal volume of 0.1 M $AlCl_3$ at 0° C. to plasma with rapid stirring will precipitate all other proteins which may then be redissolved in 0.15 N. NaCl.

EXAMPLE VIII

Figure 6:
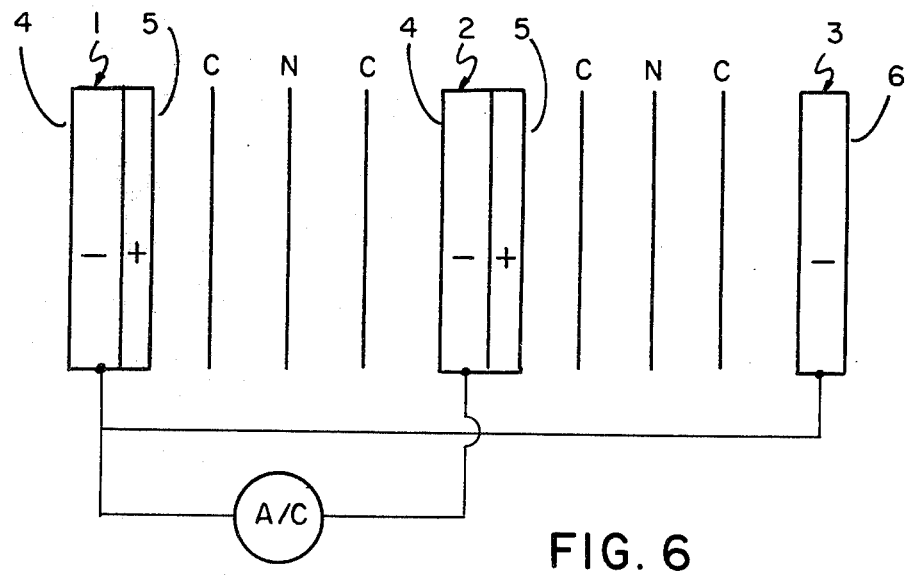

This example illustrates the use of alternating current rather than the use of direct current which is normally employed in electrodialysis operations. The stack employed a combination of neutral (N) and cation-selective (C) membranes in an arrangement illustrated in FIG. 6. An alternating current ED stack is fully described in U.S. Pat. No. 2,955,999 (C.E. Tirrell).

A valve metal such as niobium (4) plated with a noble metal such as platinum (5) is used as an anode (1) and the valve metal (60) without the coating of a noble metal is used as a cathode (3). The valve metals have the property of conducting current only when they are made cathodic, hence effecting a sort of "rectification" of the alternating current (AC). Such a stack uses two cell pairs (instead of one as used in example II) separated by a middle bipolar electrode (2) platinized (5) one one side to serve as an anode.

During the positive (+) current half cycle the platinized side (5) of electrode (1) serves as the anode and the unplatinized side (4) of electrode (2) as cathode and hence the membrane stack bound by electrodes (1) and (2) is in service whereas the membrane stack between electrodes (2) and (3) is inactive since electrode (3) being unplatinized cannot function as an anode.

During the negative (−) current half cycle the stack between electrodes (2) and (3) is functional since the platinized side (5) of electrode (2) is anode.

Such a stack operates in a similar fashion as that of example II. The apparatus will have the advantage of being operated from alternating current obviating the necessity of a rectifier. The neutral membrane can also be replaced by an anion membrane to make the operation more energy efficient.

EXAMPLE IX

This example illustrates the removal of Factor VIII from human plasma by employing electrodialysis for the desalting. The membrane separation apparatus used is a Dial-A-Cell ™ stack commercially available from Ionics, Inc, of Watertown, Mass. and is fully described in U.S. Pat. No. 4,202,772. The stack comprised two cell pairs having an effective membrane area of 13.6 $cm^2$. The ion-exchange membranes used were the cation selective (CR 61 CZL) and anion selective types (AR 103 QZL) both also obtainable from Ionics, Inc. 30 ml of fresh plasma containing ACD (anticoagulant solution consisting of a mixture of sodium citrate, citric acid and dextrose) was used in this run. The starting plasma had a Factor VIII activity of 78% of the normal. The following table summarizes the results of the desalting run. As the plasma is desalted, Factor VIII is precipitated out and hence the supernatant is depleted in Factor VIII. At about the 90% desalting level the supernatant retains about 5-10% of Factor VIII, hence the removed precipitate would contain about 90-95% of the Factor VIII originally contained in the starting plasma sample.

| Time (min.) | Conductivity (K) | % Desalting | Factor VIII activity in supernatant (% or normal) |
|---|---|---|---|
| 0 | 13.6 | 0 | 78 |
| 12 | 11.6 | 14.7 | 70 |
| 18 | 8.4 | 38.2 | 63 |
| 24 | 6.4 | 52.9 | 42 |
| 30 | 3.6 | 47.6 | 30 |
| 33 | 2.8 | 79.4 | 9 |
| 36 | 2.2 | 83.8 | 12 |
| 39 | 1.8 | 86.8 | 5 |
| 42 | 1.0 | 92.6 | 11 |

The treatment of liquid whey to increase the desirable protein content and decrease the ash (salt) and lactose components has been the object of a variety of processes. L.H. Francis in U.S. Pat. No. 3,615,664 discloses a technique in which lactose is removed from whey by concentration of the raw whey to crystallize lactose and then subjecting the supernatant to electrodialysis to effect demineralization. The same inventor in U.S. Pat. No. 3,447,930 describes another process where demineralizing is done first followed by delactosing. These and other prior art methods are directed to the purpose of obtaining a refined high protein whey end product. Some of the major concerns in carrying out these processes are denaturation of whey protein (lactalbumin) during the application of heat to effect concentration and crystallization. The process of the present invention is to overcome these problems by salting-out the whey proteins, followed by the separation and removal of the precipitated proteins by centrifugation or filtration and thereafter removal of the salt from the resulting supernatant. The supernatant will be comprised mainly of lactose and hence can be subjected to high temperatures without fear of protein denaturation. It should be noted that this process not only separates the proteins but also effects desalting by methods previously described in examples directed to plasma protein treatment.

EXAMPLE X

The ED apparatus used is similar to the one described in example I. The diluting stream is comprised of 500 ml. of supernatant obtained from a prior whey run where substantially all whey proteins were removed i.e. salted-out by electrodialysis at about a 3.5 sodium sulfate normality at an operating temperature of about 38° C. 300 ml of concentrated whey with a solid content of 22.5% (solids = 12% proteins, 80% lactose hydrate and about 8.0% ash) is used as the concentrating stream. A direct current density of about 130 ASF is used (starting CD/K = 2.0) and near the end of the run where the diluting stream becomes depleted of much of its salts, the current is adjusted to conform to a CD/K of about 4.8.

The run is continued until a normality of about 3.5 $Na_2SO_4$ is obtained in the concentrating stream where the conductivity is about 95 milli Siemens/cm. The diluting stream volume which is reduced to about 300 ml is 90% salt free and may be further treated to recover lactose. The concentrating stream which increases in volume to about 500 ml develops a fine precipitate (turbidity) of protein which is removed by centrifugation. The resulting highly salted supernatant is then used as the diluting stream to transfer its salting-out agent to a next fresh batch of concentrated whey. This method of transfering the salting-out agent is accomplished in a manner similar to the cases of human plasma protein separation as described previously.

While the invention has been herein shown and described in what is presently conceived to be the most practical and preferred embodiments thereof, it will be apparent to those of ordinary skill in the art that many modifications may be made thereof within the scope of the invention, which scope is to be accorded the broadest interpretation of the appended claims so as to encompass all equivalent assemblies and methods.

The embodiments of this invention in which an exclusive property or privilege is claimed are defined as follows:

1. A process for separating an aqueous protein mixture into fractions having intrinsically distinguishable compositions comprising removing substantially all the turbidity therefrom, subsequently, adding a salting-out agent thereto by passing said mixture at a velocity of between 3-40 cm/sec. into and out of an electrodialysis apparatus containing at least one pair of contiguous membranes defining a liquid flow chamber therebetween, impressing an electric current across said apparatus at about a CD/K=0.1 to 10 (where CD is current denisty in m-amps/$cm^2$ and K is the conductivity of the aqueous mixture in milli Siemens/cm) thereby altering the ionic environment of said mixture by increasing its ionic concentration sufficiently to at least partially destabilize one or more proteins in said mixture, allowing said destabilized protein to form turbidity, subsequently removing substantially all of said turbidity and maintaining the temperature of said mixture during the said separation in the range of between about 0°-40° C.

2. A process according to claim 1 wherein the ionic environment of said mixture is altered by increasing its ionic concentration by at least about 10 percent.

3. A process according to claim 1 wherein the ionic environment of said mixture is altered by changing its pH substantially toward the isoelectric point of at least one of the said proteins.

4. A process according to claim 1 wherein the membranes of said electrodialysis apparatus are substantially non-ion selective.

5. A process according to claim 1 wherein at least one of the said membranes in every contiguous pair is ion selective.

6. A process according to claim 1 wherein one of the membranes in every contiguous pair is cation selective.

7. A process according to claim 1 wherein one of the membranes in every contiguous pair is cation selective and the other is anion selective.

8. A process according to claim 5 wherein at least a substantial fraction of the electric current is direct current.

9. A process according to claim 1 wherein the ionic environment of said mixture is altered by substantially increasing the concentration of non-monovalent ions.

10. A process according to claim 1 wherein the ionic environment of said mixture is altered by substantially increasing the concentration of both monovalent and non-monovalent ions.

11. A process according to claim 1 wherein said subsequently removed turbidity is resolubilized.

12. A process according to claim 1 wherein said subsequently removed turbidity is at least in part resolubilized and the said resolubilized part is converted to a turbid insoluble fraction and a soluble fraction by again increasing the ionic concentration by electrodialysis and the resulting turbid insoluble and soluble fraction are separated from each other.

13. A process according to claim 1 wherein said aqueous protein mixture comprises plasma proteins and the said subsequently removed turbidity comprises fibrinogen and antihemophilic factor.

14. A process according to claim 1 wherein said aqueous protein mixture comprises substantially undenatured plasma and the said subsequently removed turbidity comprises immunoglobulins.

15. A process according to claim 1 wherein said aqueous protein mixture comprises plasma proteins, the subsequently removed turbidity comprises fibrinogen and antihemophilic factor which turbidity is resolubilized and separated into a fibrinogen rich fraction and an antihemophilic factor rich fraction by contacting with a material selected from the group consisting of ion exchange resin granules, gel permeation granules and mixtures of the same.

16. A process according to claim 1 wherein the aqueous protein mixture comprises plasma proteins and the subsequently removed trubidity comprises albumin.

17. A process according to claim 16 wherein the subsequently removed turbidity is resolubilized for use as a plasma expander.

18. A process according to claim 1 in which the aqueous protein mixture comprises plasma proteins, wherein the ionic concentration of said mixture is increased by adding, substantially non-toxic salts selected from the group consisting of sulfates, citrates, phosphates, chlorides, acetates, perchlorates, nitrates, sulfites, thiosulfates, bromides, iodides, and mixtures of these salts and the resulting turbidity comprising substantially non-albuminous proteins is removed therefrom .

19. A process for separating an aqueous protein solution comprising dispersed euglobulins and dispersed pseudoglobulins into a euglobulin rich fraction and a psuedoglobulin rich fraction comprising removing substantially all the turbidity therefrom, subsequently passing said mixture into and out of an electrodialysis apparatus containing at least one pair of contiguous membranes defining a liquid flow chamber therebetween, impressing an electric current across said apparatus thereby increasing the ionic concentration of said mixture sufficiently to result in the formation of a turbid phase relatively rich in euglobulins and relatively poor in pseudoglobulins, subsequently removing substantially all of said thus second formed turbidity, again passing the remaining aqueous mixture into and out of an electrodialysis apparatus, again imposing an electric current across said apparatus thereby further increasing the ionic concentration of the said mixture sufficiently to result in the formation of a turbid phase relatively poor in euglobulins and relatively rich in pseudoglobulins, subsequently removing substantially all of said thus third formed turbidity, again passing the remaining aqueous solution into and out of an electrodialysis apparatus and impressing an electric current across said apparatus thereby substantially decreasing the ionic concentration of the said remaining solution.

20. A process for separating an aqueous protein mixture into fractions having distinguishable compositions comprising removing substantially all the turbidity therefrom, subsequently adding by electrodialysis a salt selected from the group consisting of sulfates, citrates, acetates, phosphates, chlorides, perchlorates, nitrates, thiosulfates, sulfites, bromides, iodides, or mixtures of these salts thereby altering the ionic environment of said mixture by increasing its ionic concentration sufficiently to at least partially destabilize one or more proteins in said mixture, allowing said destabilized proteins to form turbidity, subsequently removing substantially all of said turbidity, subsequently passing the remaining supernatant at a velocity of between about 3-40 cm/sec. into and out of an electrodialysis apparatus containing at least one pair of contiguous membranes defining a liquid flow chamber therebetween, impressing an electric current across said apparatus at about a $CD/K=0.1-10$ to remove salts therein and maintaining the temperature of said mixture during said salt removl in the range of between about 0°-40° C.

21. A process according to claim 20 wherein said subsequently removed turbidity is at least partly resolubilized in electrolyte at least in part recovered by electrodialysis from said protein mixture and said resolubilized protein is then separated into at least two intrinsically distinguishable components.

22. A process according to claim 20 wherein the ionic environment of said mixture is altered by increasing its ionic concentration by at least about 10 percent.

23. A process according to claim 20 wherein the ionic environment of said mixture is further altered by changing its pH to substantially the isoelectric point of at least one of the proteins thereby resulting in the precipitation of at least said protein.

24. A process according to claim 20 wherein the salt addition is accomplished by dialysis.

25. A process according to claim 20 wherein the salt addition is accomplished through a non-ion-selective membrane.

26. A process according to claim 20 wherein the membranes of said electrodialysis apparatus are substantially non-ion-selective.

27. A process according to claim 20 wherein at least one of the said membranes in every contiguous pair is ion selective.

28. A process according to claim 20 wherein one of the membranes in every contiguous pair is cation selective.

29. A process according to claim 20 wherein one of the membranes in every contiguous pair is cation selective and the other is anion selective.

30. A process according to claim 27 wherein at least a substantial fraction of the electric current is direct current.

31. A process according to claim 20 wherein the salts removed by the electrodialysis apparatus from said remaining supernatant is again added to a subsequent protein mixture to cause formation of turbidity.

32. A process according to claim 20 wherein the aqueous protein mixture comprises plasma proteins the the said subsequently removed turbidity comprises fibrinogen and antihemophilic factor.

33. A process according to claim 20 wherein the aqueous protein mixture comprises substantially undenatured plasma proteins and the said subsequently removed turbidity comprises immunoglobulins.

34. A process according to claim 20 wherein the final product of the electrodialysis treatment is a substantially salt free albumin.

35. A process according to claim 34 wherein an outside source of salt is added to the substantially salt free albumin to obtain the required electrolyte balance suitable for intravenous applications.

36. The process according to claim 1 wherein said aqueous protein mixture comprises whey.

37. A process according to claim 1 wherein said aqueous protein mixture comprises plasma proteins and the said subsequently removed turbidity comprises antihemophilic factor.

* * * * *